United States Patent
Wang et al.

(10) Patent No.: US 10,821,146 B2
(45) Date of Patent: Nov. 3, 2020

(54) POWDER FORMULATION HAVING A FUNCTION OF ENHANCING IMMUNITY AND METHOD FOR PREPARING THE SAME

(71) Applicant: INFINITUS (CHINA) COMPANY LTD., Jiang Men, Guangdong (CN)

(72) Inventors: Lei Wang, Guangdong (CN); Ruiqi He, Guangdong (CN); Hongwei Zhao, Guangdong (CN); Qingtao Tang, Guangdong (CN)

(73) Assignee: INFINITUS (CHINA) COMPANY LTD., Jiang Men, Guangdong (CN)

( * ) Notice: Subject to any disclaimer, the term of this patent is extended or adjusted under 35 U.S.C. 154(b) by 275 days.

(21) Appl. No.: 16/024,870

(22) Filed: Jul. 1, 2018

(65) Prior Publication Data

US 2019/0125813 A1 May 2, 2019

(30) Foreign Application Priority Data

Oct. 26, 2017 (CN) .......................... 2017 1 1013094

(51) Int. Cl.
| | | |
|---|---|---|
| *A61K 36/00* | (2006.01) | |
| *A61K 36/076* | (2006.01) | |
| *A61K 9/00* | (2006.01) | |
| *A61K 31/733* | (2006.01) | |
| *A61K 36/07* | (2006.01) | |
| *A61K 36/815* | (2006.01) | |
| *A61K 36/605* | (2006.01) | |
| *A61K 36/77* | (2006.01) | |
| *A61K 36/48* | (2006.01) | |
| *A61K 38/16* | (2006.01) | |
| *A61K 36/8994* | (2006.01) | |
| *A61K 36/185* | (2006.01) | |
| *A61K 36/725* | (2006.01) | |
| *A61P 37/04* | (2006.01) | |
| *A23L 33/105* | (2016.01) | |
| *A23P 10/40* | (2016.01) | |
| *A61K 9/14* | (2006.01) | |

(52) U.S. Cl.
CPC .......... *A61K 36/076* (2013.01); *A23L 33/105* (2016.08); *A23P 10/40* (2016.08); *A61K 9/0056* (2013.01); *A61K 9/14* (2013.01); *A61K 31/733* (2013.01); *A61K 36/07* (2013.01); *A61K 36/185* (2013.01); *A61K 36/48* (2013.01); *A61K 36/605* (2013.01); *A61K 36/725* (2013.01); *A61K 36/77* (2013.01); *A61K 36/815* (2013.01); *A61K 36/8994* (2013.01); *A61K 38/168* (2013.01); *A61P 37/04* (2018.01); *A23V 2002/00* (2013.01); *A61K 2236/331* (2013.01); *A61K 2236/51* (2013.01); *A61K 2236/53* (2013.01)

(58) Field of Classification Search
None
See application file for complete search history.

(56) References Cited

FOREIGN PATENT DOCUMENTS

| CN | 101496603 A | 8/2009 |
|---|---|---|
| CN | 102178235 A | 9/2011 |
| CN | 104719917 A | 6/2015 |
| CN | 105942126 A | 9/2016 |
| CN | 107136509 A | 9/2017 |
| CN | 107252114 A | 10/2017 |
| CN | 107259571 A * | 10/2017 |

OTHER PUBLICATIONS

Guanting Ling, Health food ingredients manual, The second edition, Chemical industry press, pp. 13-17, May 31, 2007.
The 1st Office Action dated Mar. 3, 2020 for the Chinese priority patent application CN201711013094.6.
Gong Qiang et al, Effect of Inulin on Modulating Immune Function in Mice, Food Science2016, vol. 37, No. 07 (Henan Engineering Research Center of Food Material, College of Food and Bioengineering, Henan University of Science andTechnology, Luoyang 471023, China).
Wang Bailing, Research progress on pharmacological action of Polysaccharide from Auricularia auricular,China Medical Herald, vol. 13, No. 26, pp. 29-32, Sep. 2016.
Liu Hui-zhi,A Review on Separation and Medicinal Value of Active Pharmaceutical Ingredients from Poria cocos, Edible Fungi of China,vol. 34 No. 6, pp. 1-6, Sep. 2015.
Ma Qianqian, Research Progress in Biological Activities of Lycium barbarum Polysaccharides, Farm Products Processing, No. 7, pp. 59-61, 66, Jul. 2017.
Xie Xiao-hua, Development of the Studies on Chemical Constituents and Effects of Mulberry, Journal of Jilin Engineering Normal University, vol. 33 No. 9, pp. 85-87, Sep. 2017.
Su Dong-xiao, Effects of Water Soluble Extracts from Longan on Immune Regulation in Normal Mice, Scientia Agricultura Sinica, vol. 43 No. 9, pp. 1919-1925,Sep. 19. 2010.

(Continued)

*Primary Examiner* — Qiuwen Mi
(74) *Attorney, Agent, or Firm* — Yue (Robert) Xu; Apex Attorneys at Law, LLP

(57) ABSTRACT

The present disclosure belongs to the field of health care products, disclosing a powder formulation made from inulin, Auricularia, PORIA, LYCII FRUCTUS, MORI FRUCTUS, LONGAN ARILLUS, soy peptide powder, COICIS SEMEN, NELUMBINIS SEMEN and JUJUBAE FRUCTUS. The starting materials of the powder formulation are all from natural Chinese herbal medicine without addition of excipient. In addition, dose required for the powder formulation is small; it is easy to be taken and can be dissolved in water; it is soluble in cold water and can be absorbed quickly. The method for preparing the powder formulation in the present disclosure is simple and suitable for large-scale production. The powder formulation obtained has a good stability, long storage time, good taste. Experiments show that the powder formulation of the present disclosure can significantly enhance immunity, therefore can be used to prepare the health care foods having function on improving immunity.

5 Claims, No Drawings

(56) References Cited

OTHER PUBLICATIONS

Fu xiaoyi, Progress on Immunological Regulation of Soybean Peptides, Soybean science & technology, No. 1, pp. 38-42, Feb. 25, 2014.
Zhang Jinmei, Research-progress-on-chemical-constituents-and-pharmaceutical-activities-of-Coix-lacryma-jobi-L., Chinese Pharmaceutical Journal, vol. 37 No. 1, Jan. 2012.
Zeng Shaoxiao, Advances in the Bioactivity of Lotus-seed, Chinese Journal of Tropical Crops, vol. 33 No. 11, pp. 2110-2114, Nov. 2012.
Jong Li-jun, Effect of jujube juice concentrate on relieve physical fatigue and immune function in mice, science and technology of Food Industry, No. 12, pp. 314-318, Mar. 7, 2017.

\* cited by examiner

… (1)

POWDER FORMULATION HAVING A FUNCTION OF ENHANCING IMMUNITY AND METHOD FOR PREPARING THE SAME

CROSS REFERENCE TO RELATED APPLICATIONS

This application claims the priority of Chinese Patent Application No. 201711013094.6, filed on Oct. 26, 2017, and the disclosures of which are hereby incorporated by reference.

FIELD

The present invention relates to the field of health care products, specifically to a powder formulation having a function of enhancing immunity and method for preparing the same, especially to a powder formulation mainly made from natural Chinese herbal medicine and having a function of enhancing immunity, and method for preparing the same.

BACKGROUND

Immunity is the defense mechanism of human body. It is the ability that human body recognizes and eradicates any of the foreign objects (virus, bacteria and so on) from the external, processes the senescent, injured, dead or denatured body cells, and recognizes and processes the mutant cells and cells infected by virus in human body. With accelerating pace of modern life, continuously increasing work pressure, unbalanced diet, insufficiency sleep, lack of exercise and so on are easy to cause low immunity in people. Body with low immunity is easy to be infected or get cancer and the immune system cannot play the role of protection normally. In this case, the body is easy to be infected by bacteria, virus, fungi and so on, and therefore the most direct manifestation of low immunity is easy to get sick. Due to frequent sickness, consumption of body is aggravated, symptoms such as weak constitution, malnutrition, listlessness, fatigue, loss of appetite, sleep disorder and so on often occur. Illness, injections and medication become routine, and it takes a long time to recover from sick every time. In addition, the recurrent illness, such as recurrent cold, recurrent tonsillitis, recurrent asthma, recurrent bronchitis, recurrent pneumonia and recurrent diarrhea, in a long term, will not only lead to poor physical and mental development, but also induce serious diseases.

People's living standard has increased significantly in recent years, and consumption concept and health concept of people have changed a lot. In order to avoid the adverse effects of unhealthy, people pay more and more attention to the use of nutraceuticals. Currently, the health care foods for enhancing immunity are mainly supplements with vitamins and minerals, and most of them are in the form of oral liquid. Oral liquid has disadvantages of inconvenience of carrying, poor stability and short storage time. Large doses of adjuvants such as starch and hydroxymethyl cellulose are often added to the tablet when the tablets are made, which causes a long disintegration time. At the same time, it is inconvenient for people who have dysphagia, such as old people and children.

SUMMARY

In view of above, in order to overcome the deficiencies in the prior art, an object of the present disclosure is to provide a powder formulation having a function of enhancing immunity and method for preparing the same. In the present disclosure, the powder formulation having a function of enhancing immunity is mainly made from natural Chinese herbal medicine, therefore the powder formulation has natural components and without addition of excipients.

In order to achieve the goal of the present disclosure, the following technical solutions are used in the present disclosure.

A powder formulation, which has the ability of enhancing immunity, is made from inulin, Auricularia, PORIA, LYCII FRUCTUS, MORI FRUCTUS, LONGAN ARILLUS, soy peptide powder, COICIS SEMEN, NELUMBINIS SEMEN and JUJUBAE FRUCTUS as starting materials.

Further, as preferred, the mass ratio of inulin, Auricularia, PORIA, LYCII FRUCTUS, MORI FRUCTUS, LONGAN ARILLUS, soy peptide powder, COICIS SEMEN, NELUMBINIS SEMEN and JUJUBAE FRUCTUS is (20 to 60):(10 to 15):(10 to 15):(10 to 15):(5 to 10):(5 to 8):(1 to 4):(0.1 to 0.5):(0.1 to 0.5):(0.1 to 0.5).

In some embodiments, the mass ratio of inulin, Auricularia, PORIA, LYCII FRUCTUS, MORI FRUCTUS, LONGAN ARILLUS, soy peptide powder, COICIS SEMEN, NELUMBINIS SEMEN and JUJUBAE FRUCTUS is 20:15:10:15:5:8:1:0.5:0.1:0.5.

In some embodiments, the mass ratio of inulin, Auricularia, PORIA, LYCII FRUCTUS, MORI FRUCTUS, LONGAN ARILLUS, soy peptide powder, COICIS SEMEN, NELUMBINIS SEMEN and JUJUBAE FRUCTUS is 60:10:10:10:10:5:4:0.1:0.5:0.5.

In some embodiments, the mass ratio of inulin, Auricularia, PORIA, LYCII FRUCTUS, MORI FRUCTUS, LONGAN ARILLUS, soy peptide powder, COICIS SEMEN, NELUMBINIS SEMEN and JUJUBAE FRUCTUS is 40:12:12:12:8:6:2:0.3:0.3:0.3.

The present disclosure also provides a method for preparing the powder formulation, comprising: adding water to Auricularia, PORIA, LYCII FRUCTUS, MORI FRUCTUS, LONGAN ARILLUS, COICIS SEMEN, NELUMBINIS SEMEN and JUJUBAE FRUCTUS for extraction; collecting the extract upon filtration; adding inulin and soy peptide powder, mixing, drying and granulating the powders.

Preferably, in the method for preparing the powder formulation of the present disclosure, the extraction is a decoction extraction.

Preferably, the extraction is performed by: adding water which is 7 to 15 times the weight of the starting materials and extracting for 1.5 to 3 hours in a first extraction; and adding water which is 6 to 14 times the weight of the starting materials and extracting for 0.5 to 4 hours in a second extraction.

Preferably, the drying in the method of the present disclosure is selected from the group consisting of spray drying, freeze drying, belt drying, microwave drying and vacuum drying.

Preferably, the method further comprises a concentration step prior to the adding of inulin and soy peptide powder. Preferably, the concentration is vacuum concentration or reverse osmosis concentration.

Preferably, the particle size of product provided by the method in the present disclosure is controlled below 35-mesh.

The present disclosure provides use of the powder formulation in the manufacture of health care food having a function of enhancing immunity.

It can be concluded from the above technical solutions that the present disclosure provides a powder formulation made from inulin, Auricularia, PORIA, LYCII FRUCTUS, MORI FRUCTUS, LONGAN ARILLUS, soy peptide powder, COICIS SEMEN, NELUMBINIS SEMEN and JUJUBAE FRUCTUS. The starting materials of the powder formulation are all from natural Chinese herbal medicine without addition of excipients. It is clean and has natural components, in line with people's pursuit of natural and health foods. In addition, dose required for the powder formulation is small; it is easy to be taken and can be dissolved in water; it is soluble in cold water and can be absorbed quickly. The method for preparing the powder formulation in the present disclosure is simple and suitable for large-scale production. Also, it is easy to be carried. The powder formulation obtained has a good stability, long storage time, good taste. It melts in mouth and is soluble in cold water. Experiments show that the powder formulation of the present disclosure can significantly enhance immunity, therefore can be used to prepare the health care foods having a function of enhancing immunity.

DETAILED DESCRIPTION

The present disclosure discloses a powder formulation having a function of enhancing immunity and method for preparing the same. One of ordinary skill in the art can learn from the contents herein and improve the process parameters appropriately. In particular, it shall be noted that all the similar substitutions and modifications are apparent to one of ordinary skill in the art and are to be considered within the scope of the present invention. The method and product of the present invention have been described with preferred examples. It is apparent that one of the ordinary skills in the art can make change or modify the combination to the method and product of the present invention without departing from the spirit, scope and spirit of the invention, therefore realizing and applying the techniques of the present invention.

In order to understand the present disclosure further, the technical solutions in the embodiments of the present disclosure will be described clearly and completely herein in conjunction with the examples of the present disclosure. Apparently, the described examples are only a part of the examples of the present disclosure, rather than all examples. Based on the examples in the present disclosure, all of other examples, made by one of ordinary skill in the art without any creative efforts, fall into the protection scope of the present disclosure.

Without special illustration, all the reagents in the examples of the present disclosure are commercial products, which can be purchased on the market.

EXAMPLES

Example 1: Heath Care Powder Formulation of the Present Disclosure

Formulation:

| | |
|---|---|
| Inulin | 20 g |
| Auricularia | 15 g |
| PORIA | 10 g |
| LYCII FRUCTUS | 15 g |
| MORI FRUCTUS | 5 g |
| LONGAN ARILLUS | 8 g |
| Soy Peptide Powder | 1 g |
| COICIS SEMEN | 0.5 g |
| NELUMBINIS SEMEN | 0.1 g |
| JUJUBAE FRUCTUS | 0.5 g |

Preparation Method:

Auricularia, PORIA, LYCII FRUCTUS, MORI FRUCTUS, LONGAN ARILLUS, COICIS SEMEN, NELUMBINIS SEMEN and JUJUBAE FRUCTUS as starting materials were put into an extracting tank and purified water 8 times the weight of the starting materials was added. Extraction was performed for 4 hours, followed by filtration. Purified water 6 times the weight of the starting materials was added again and extraction was performed for 4 hours, followed by filtration. The two filtrates were combined and concentrated. Inulin and soy peptide powder were added, and spray drying or belt drying or freeze drying was carried out to obtain a dry powder of Chinese herbal medicine extract. The dry powder was granulated and the particle size of the powder was controlled below 35-mesh.

Example 2: Heath Care Powder Formulation of the Present Disclosure

Formulation:

| | |
|---|---|
| Inulin | 60 g |
| Auricularia | 10 g |
| PORIA | 10 g |
| LYCII FRUCTUS | 10 g |
| MORI FRUCTUS | 10 g |
| LONGAN ARILLUS | 5 g |
| Soy Peptide Powder | 4 g |
| COICIS SEMEN | 0.1 g |
| NELUMBINIS SEMEN | 0.5 g |
| JUJUBAE FRUCTUS | 0.1 g |

Preparation Method:

Auricularia, PORIA, LYCII FRUCTUS, MORI FRUCTUS, LONGAN ARILLUS, COICIS SEMEN, NELUMBINIS SEMEN and JUJUBAE FRUCTUS as starting materials were put into extracting tank and purified water 15 times the weight of the starting materials was added. Extraction was performed for 1.5 hours, followed by filtration. Purified water 14 times the weight of the starting materials was added and extraction was performed for 0.5 hour, followed by filtration. The two filtrates were combined and concentrated. Inulin and soy peptide powder were added, and spray drying or belt drying or freeze drying was carried out to obtain a dry powder of Chinese herbal medicine extract. The dry powder was granulated and the particle size of the powder was controlled below 35-mesh.

Example 3: Heath Care Powder Formulation of the Present Disclosure

Formulation:

| | |
|---|---|
| Inulin | 40 g |
| Auricularia | 12 g |
| PORIA | 12 g |
| LYCII FRUCTUS | 12 g |
| MORI FRUCTUS | 8 g |
| LONGAN ARILLUS | 6 g |
| Soy Peptide Powder | 2 g |
| COICIS SEMEN | 0.3 g |

-continued

| | |
|---|---|
| NELUMBINIS SEMEN | 0.3 g |
| JUJUBAE FRUCTUS | 0.3 g |

Preparation Method:

Auricularia, PORIA, LYCII FRUCTUS, MORI FRUCTUS, LONGAN ARILLUS, COICIS SEMEN, NELUMBINIS SEMEN and JUJUBAE FRUCTUS as starting materials were added to purified water 10 times the weight of the starting materials. Extraction was performed for 2 hours, followed by filtration. Purified water 10 times the weight of the starting materials was added and extraction was performed for 2.5 hours, followed by filtration. The two filtrates were combined and concentrated. Inulin and soy peptide powder were added, and spray drying or belt drying or freeze drying was carried out to obtain a dry powder of Chinese herbal medicine extract. The dry powder was granulated and the particle size of the powder was controlled below 35-mesh.

Experimental Example 1: Immunity Enhancing Test

The enhancement of immunity function is evaluated by four aspects including cellular immune function, humoral immune function, monocyte-macrophage function and NK cell activity. The test sample is regarded as having a function of enhancing immunity if any two aspects show positive results.

1. Test sample: the powder formulation prepared in Example 3.
2. Experimental animals: Balb/C inbred strain mouse, male, 18 to 22 g of each mouse. The mice were adoptive fed for a week and divided into groups (12 per group) randomly according to their body weights.
3. Grouping and Time of Administration of the Test Sample Test animals were divided into 4 groups, i.e., a control group (administrated with distilled water) and 3 treatment groups including low-dose group, medium-dose group and high-dose group, wherein the treatment groups were given 5 times (166.67 mg/kg), 10 times (333.33 mg/kg) and 30 times (1000 mg/kg) of the human recommended amount of the test sample, respectively, three repetitions per dose. The test sample was given for 30 days.

4. Experiment Methods and Results
4.1 Effect of the Test Sample on the Body Weight of Balb/C Mice

TABLE 1

Effect of the test sample on the body weight of Balb/C mice

| Group (g/kg · BW) | Original Weight (average ± standard deviation) | Final Weight (average ± standard deviation) |
|---|---|---|
| Control Group | 17.24 ± 1.70 | 25.71 ± 2.13 |
| Low-dose Group | 17.67 ± 1.37 | 25.34 ± 1.12 |
| Medium-dose Group | 17.29 ± 1.52 | 25.96 ± 1.11 |
| High-dose Group | 17.57 ± 2.00 | 26.67 ± 1.33 |

Table 1 showed that 30 days after the administration of test sample at different doses orally, the weight of the mice in three treatment groups did not show significant differences compared with that of the control group (P>0.05), indicating that the test sample was safe.

4.2 Effect of the Test Sample on Spleen/Body Weight Ratio of Balb/C Mice

TABLE 2

Effect of the test sample on spleen/body weight ratio of Balb/C mice

| Group (g/kg · BW) | Spleen/Weight ratio (%) | P |
|---|---|---|
| Control Group | 0.33 ± 0.02 | — |
| Low-dose Group | 0.46 ± 0.13** | 0.0056 |
| Medium-dose Group | 0.41 ± 0.02** | 7.12E−08 |
| High-dose Group | 0.45 ± 0.06** | 9.03E−05 |

Table 2 showed that 30 days after the administration of test sample at different doses orally, the spleen/body weight ratio of three treatment groups showed significant differences compared with that of the control group (P<0.05). The test sample significantly increased the spleen/body weight ratio.

4.3 Effect of the Test Sample on Transformation of ConA-Induced Lymphocyte Cells (1) Preparation of spleen cells suspension. Spleen was removed under sterile condition and placed in Hanks solution. The spleen was snipped into pieces by a tweezers to prepare a single cell suspension, which was passed a 200-mesh screen. The cells were washed with Hanks solution twice through 10 min centrifugation (1000 rpm/min) each time. The cell suspension was suspended in the complete medium and the cell density was adjusted to $3\times10^6$/ml after counting the number of viable cells by trypan blue staining.

(2) Spleen cell proliferation test. Each of the cell suspension was divided into two parts and added into 24-well plate, 1 mL per well. ConA solution (final concentration of 7.5 μg/mL) was added into one well, and the other well was set as the control. Cells were incubated in an incubator for 72 h. MTT method was used to measure the absorbance OD value of each well.

TABLE 3

Effect of the test sample on transformation of ConA-induced lymphocyte cells

| Group (g/kg · BW) | Optical Density Difference | P |
|---|---|---|
| Control Group | 0.776 ± 0.101 | — |
| Low-dose Group | 0.776 ± 0.402 | 0.999 |
| Medium-dose Group | 0.835 ± 0.081 | 0.706 |
| High-dose Group | 1.553 ± 0.143 | <0.001 |

The results in Table 3 showed that, 30 days after the administration of test sample at different doses orally, with the increase of the dose, the transformation rate of lymphocyte cells increased gradually in comparison with the control group. The high-dose group showed significant effect on ConA-induced lymphocyte transformation (P<0.01). The experiment result was positive.

4.4 Delayed-Type Hypersensitivity (DTH)

Dinitrofluorobenzene-Induced Mouse DTH (Ear Swelling Assay)

(1) Preparation of DNFB Solution (1% of Dinitrofluorobenzene)

(2) Sensitization: the fur on abdomen of each mouse was shaved by barium sulfate at an area about $3\times3$ cm$^2$, 50 μL DNFB solution was applied evenly to induce hypersensitivity.

(3) Development and measure of DTH: 5 days later, DNFB solution was applied evenly on both sides of the right ear of the mice for stimulation. The mice were sacrificed by cervical dislocation 24 h later. Two ears were cut off, and a piece with diameter of 8 mm was taken by a puncher and weighted.

Results: DTH level was determined by mass differences between the left ear and the right ear, which was shown in Table 4.

TABLE 4

Effect of the test sample on mouse ear swelling

| Group (g/kg · BW) | Mass difference between left ear and right ear (mg‰) | P |
|---|---|---|
| Control Group | 17.09 ± 3.49 | — |
| Low-dose Group | 15.02 ± 3.46 | 0.22 |
| Medium-dose Group | 15.58 ± 2.78 | 0.32 |
| High-dose Group | 16.44 ± 3.96 | 0.72 |

Table 4 shows that, there was no significant mass differences between left ear and right era between three treatment groups and the control group (P>0.05), therefore the result was negative.

4.5 Antibody-Producing Cell Test (Modified Jerne's Slide Method)

(1) Preparation of spleen cells suspension. The mice were sacrificed by cervical dislocation 4 to 5 days after SRBC immunization. Spleen was removed and prepared into spleen cells suspension. The cell density was adjusted to $5 \times 10^6$ cell/mL.

(2) Plaque assay. The surface culture medium was dissolved, placed in 45° C. water bath and mixed with the same amount of 2×Hanks solution (pH of 7.2). The medium was divided into aliquot in test tubes, 0.5 mL per tube. 50 μL of 10% SRBC and 20 μL of spleen cells suspension were added into the tube, mixed homogenously and rapidly. The mixture was poured on a glass slide with a thin layer of agarose. Control slide was prepared in parallel. After solidification, the glass slides were placed (upside down) in a slide box and incubated for 1.5 h. The statistic results of hemolytic plaque were shown in Table 5.

TABLE 5

Effect of the test sample on antibody-producing cells

| Group (g/kg · BW) | Number of plaque/spleen cells ($1 \times 10/10^6$) | P |
|---|---|---|
| Control Group | 426.63 ± 49.12 | — |
| Low-dose Group | 389.05 ± 23.58 | 0.05 |
| Medium-dose Group | 401.90 ± 57.39 | 0.34 |
| High-dose Group | 511.60 ± 58.19 | <0.01 |

Table 5 showed that, 30 days after the administration of the test sample at different doses orally, low-dose group and medium-dose group have no significant difference in the plaque number in comparison with the control group. The plaque number of the high-dose group showed a significant difference (P<0.01) from that of the control group, so the experiment result was positive.

4.6 NK Cell Activity Assay (Lactate Dehydrogenase Assay)

Passage of target cell (YAC-1 cell): before the experiments, target cells were subcultured and cell conditions were adjusted.

The preparation method for spleen cells suspension was the same as that of 4.3. Cell viability was above 95% based on trypan blue staining. The density of the separated spleen cells suspension was adjusted to $2 \times 10^7$ cell/mL.

NK cell activity assay: 100 μL of target cells and 100 μL of effector cells (effector cells: target cells=50:1) were added into 96-well plate. Spontaneously releasing well contained 100 μL of target cell and 100 μL of culture medium, while maximally releasing well contained 100 μL of 1% NP40 or 100 μL of 2.5% Triton. Each experiment has three repetitions. The cells were incubated in an incubator for 4 hours. Thereafter, the culture plate was subjected to a 5 min low-speed centrifugation and 100 μL of suspension from each well was transferred to a flat-bottom 96-well plate. OD value of each well at 490 nm was measured by LDH assay kit. NK cell activity was calculated by the average value of the three repeat wells in each group, and the results were shown in FIG. 4. Formula for calculating NK cell activity was as follows: NK cell activity (%)=(OD value of reaction well-OD value of spontaneously releasing well)/(OD value of maximally releasing well-OD value of spontaneously releasing well)

TABLE 6

Effect of the test sample on NK cell activity

| Group (g/kg · BW) | NK Cell Activity | P |
|---|---|---|
| Control Group | 36.95 ± 3.46 | — |
| Low-dose Group | 31.96 ± 5.71 | 0.07 |
| Medium-dose Group | 32.54 ± 8.95 | 0.20 |
| High-dose Group | 49.17 ± 11.36 | 0.02 |

Table 6 showed that, 30 days after the administration of the test sample at different doses orally, compared with the control group, the NK cell activity of the low-dose group and medium-dose group have no significant difference (P>0.05), but the NK cell activity of the high-dose group showed significant difference (P<0.05). The experiment result was positive.

4.7 Phagocytosis Experiment of Mouse Abdominal Macrophage on Chicken Red Blood Cell (Drop-Slide Method)

Activation of mouse macrophage. 4 days before the experiment, 0.2 mL of 2% sheep red blood cells were injected to the abdomen of each mouse. The mice were sacrificed by cervical dislocation. 4 mL of Hanks solution containing calf serum was injected into the abdomen of each mouse and the abdominal macrophages were washed out by gently massage of the abdomen 20 times. A small outlet was cut on the abdominal wall, 2 mL of abdominal washing liquid was sucked out by a dropper. 0.5 mL of abdominal washing liquid was pippetted to the tube containing 0.5 mL of 1% chicken red blood cell suspension and mixed evenly. 0.5 mL of the mixture was added into the agarose circle on a glass slide. The slide was incubated in an incubator for 20 min. The non-adhered cells were rinsed off by physiological saline as soon as the incubation finished. The cells were fixed by methanol for 1 min and stained by Giemsa for 15 min. Thereafter, the slide was rinsed and dried. The percentage of phagocytosis and phagocytic index were counted under a microscope with 40× magnification. The results were shown in FIG. 5. Number of macrophages was counted under oil immersion lens, and there were 100 cells were counted on each slide. The formula for calculating percentage of phagocytosis and phagocytic index were as follows:

Percentage of phagocytosis (%)=number of macrophage containing chicken red blood cell/number of counted macrophage×100

Phagocytic index=total number of the swallowed chicken red blood cell/number of counted macrophage

TABLE 7

Effect of the test sample on phagocytic activity of mice macrophages

| Group (g/kg · BW) | Phagocytosis Percentage (%) | | Phagocytic Index | |
|---|---|---|---|---|
| | Numerical Value | P | Numerical Value | P |
| Control Group | 15.45 ± 2.89 | — | 0.25 ± 0.04 | — |
| Low-dose Group | 16.40 ± 3.23 | 0.62 | 0.25 ± 0.07 | 0.999 |
| Medium-dose Group | 15.32 ± 1.75 | 0.93 | 0.31 ± 0.10 | 0.21 |
| High-dose Group | 24.22 ± 2.86 | <0.01 | 0.39 ± 0.05 | <0.01 |

Table 7 showed that, 30 days after the administration of the test samples at different doses orally, compared with the control group, the percentage of phagocytosis and phagocytic index of low-dose group and medium-dose group have no significant differences (P>0.05), but the percentage of phagocytosis and phagocytic index of high-dose group showed significant difference (P<0.05). The experiment result was positive.

5. Conclusion 5.1 The results of mouse lymphocyte transformation experiment is positive and delayed-type hypersensitivity reaction is negative, indicating that the result of cell immune function test is positive.

5.2 The result of antibody-producing cell test is positive, indicating that the result of humoral immune function test is positive.

5.3 The result of phagocytosis experiment of mouse abdominal macrophage on chicken red blood cell is positive, indicating that the result of monocyte-macrophage function test is positive.

5.4 The result of lactate dehydrogenase assay is positive, indicating that the result of NK cell activity is positive.

In these four aspects of the animal experiments, cell immune function, humoral immune function, monocyte-macrophage function and NK cell activity tests, the results show that the high-dose group significantly improves the lymphocyte transformation, phagocytosis of abdominal macrophage, NK cell activity and antibody production, indicating that high-dose test sample has immunity enhancing function.

The powder formulations obtained in Example 1 and Example 2 have a similar effect as that of Example 3.

What is claimed is:

1. A method of enhancing immunity comprising administering a powder formulation to a subject in need thereof, wherein the powder formulation is made from inulin, Auricularia, PORIA, LYCII FRUCTUS, MORI FRUCTUS, LONGAN ARILLUS, soy peptide powder, COICIS SEMEN, NELUMBINIS SEMEN and JUJUBAE FRUCTUS as starting materials, and wherein the mass ratio of inulin, Auricularia, PORIA, LYCII FRUCTUS, MORI FRUCTUS, LONGAN ARILLUS, soy peptide powder, COICIS SEMEN, NELUMBINIS SEMEN and JUJUBAE FRUCTUS is (20 to 60):(10 to 15):(10 to 15):(10 to 15):(5 to 10):(5 to 8):(1 to 4):(0.1 to 0.5):(0.1 to 0.5):(0.1 to 0.5).

2. The method according to claim 1, wherein the mass ratio of inulin, Auricularia, PORIA, LYCII FRUCTUS, MORI FRUCTUS, LONGAN ARILLUS, soy peptide powder, COICIS SEMEN, NELUMBINIS SEMEN and JUJUBAE FRUCTUS is 20:15:10:15:5:8:1:0.5:0.1:0.5.

3. The method according to claim 1, wherein the mass ratio of inulin, Auricularia, PORIA, LYCII FRUCTUS, MORI FRUCTUS, LONGAN ARILLUS, soy peptide powder, COICIS SEMEN, NELUMBINIS SEMEN and JUJUBAE FRUCTUS is 60:10:10:10:10:5:4:0.1:0.5:0.5.

4. The method according to claim 1, wherein the mass ratio of inulin, Auricularia, PORIA, LYCII FRUCTUS, MORI FRUCTUS, LONGAN ARILLUS, soy peptide powder, COICIS SEMEN, NELUMBINIS SEMEN and JUJUBAE FRUCTUS is 40:12:12:12:8:6:2:0.3:0.3:0.3.

5. The method according to claim 1, wherein the powder formulation is in the form of health care food.

* * * * *